United States Patent
Mishina et al.

(10) Patent No.: US 11,160,744 B2
(45) Date of Patent: Nov. 2, 2021

(54) GEL COMPOSITION

(71) Applicant: SHOWA DENKO K.K., Tokyo (JP)

(72) Inventors: Natsuno Mishina, Yokohama (JP); Naoko Ito, Tokorozawa (JP); Manami Hatano, Urayasu (JP); Risa Iguchi, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/754,015

(22) PCT Filed: Oct. 5, 2018

(86) PCT No.: PCT/JP2018/037423
§ 371 (c)(1),
(2) Date: Apr. 6, 2020

(87) PCT Pub. No.: WO2019/073930
PCT Pub. Date: Apr. 18, 2019

(65) Prior Publication Data
US 2020/0323759 A1 Oct. 15, 2020

(30) Foreign Application Priority Data
Oct. 11, 2017 (JP) .............................. JP2017-197603

(51) Int. Cl.
*A61K 8/55* (2006.01)
*A61K 8/02* (2006.01)
*A61K 8/19* (2006.01)
*A61K 8/73* (2006.01)

(52) U.S. Cl.
CPC .............. *A61K 8/55* (2013.01); *A61K 8/0212* (2013.01); *A61K 8/19* (2013.01); *A61K 8/73* (2013.01)

(58) Field of Classification Search
CPC ........... A61K 8/0212; A61K 8/19; A61K 8/73
See application file for complete search history.

(56) References Cited

U.S. PATENT DOCUMENTS

| | | | |
|---|---|---|---|
| 8,652,511 B2 * | 2/2014 | Cottrell | A61K 31/355 424/449 |
| 9,975,999 B2 * | 5/2018 | Tamura | A61Q 15/00 |
| 2010/0221306 A1 * | 9/2010 | Tsujihata | A61K 8/35 424/443 |
| 2017/0143608 A1 | 5/2017 | Saeki | |

FOREIGN PATENT DOCUMENTS

| | | |
|---|---|---|
| CN | 106963706 A | 7/2017 |
| EP | 2692336 A1 | 2/2014 |
| JP | 2002-87993 A | 3/2002 |
| JP | 2006-8616 A | 1/2006 |
| JP | 2007-176886 A | 7/2007 |
| JP | 2009-73764 A | 4/2009 |
| JP | 2012-214454 A | 11/2012 |
| JP | 2013-155171 A | 8/2013 |
| JP | 2016-50196 A | 4/2016 |
| JP | 2017-57146 A | 3/2017 |
| WO | 01/02478 A1 | 1/2001 |
| WO | 03/000787 A1 | 1/2003 |
| WO | 226100 | * 9/2010 |
| WO | WO 2012133409 | * 10/2012 |
| WO | WO 2016031634 | * 3/2016 |
| WO | 2016222612 | * 12/2016 |

OTHER PUBLICATIONS

International Search Report for PCT/JP2018/037423 dated Jan. 8, 2019 (PCT/ISA/210).
Extended European Search Report dated Jun. 16, 2021 from the European Patent Office in EP Application No. 18865742.3.

* cited by examiner

*Primary Examiner* — Shirley V Gembeh
(74) *Attorney, Agent, or Firm* — Sughrue Mion, PLLC

(57) ABSTRACT

A gel composition containing (a) at least one selected from tocopherol phosphoric acid esters and salts thereof; (b) carrageenan; (c) locust bean gum; (d) at least one selected from agar and glucomannan; and e) water.

14 Claims, No Drawings

GEL COMPOSITION

CROSS REFERENCE TO RELATED APPLICATIONS

This application is a National Stage of International Application No. PCT/JP2018/037423 filed Oct. 5, 2018, claiming priority based on Japanese Patent Application No. 2017-197603 filed on Oct. 11, 2017.

TECHNICAL FIELD

The present invention relates to a gel composition. In particular, the present invention relates to a gel composition suitable for a pack cosmetic such as an eye pack cosmetic.

Priority is claimed on Japanese Patent Application No. 2017-197603, filed on Oct. 11, 2017, the content of which is incorporated herein by reference.

BACKGROUND ART

Conventionally, a sheet-shaped external preparation that is applied to skin for use has been used for the purpose of imparting a beauty effect. As a cosmetic pack, a hydrogel-form masking pack preparation for cosmetic use that contains shirasu, hot spring water, or the like and multiply exhibits a skin brightening effect, a wrinkle ameliorating effect, a moisturizing effect, and a nutritional effect (Patent Literature 1), an external preparation kit excellent in water separation rate, elongation rate, and solubility of a water-soluble sheet (Patent Literature 2), or a adhesive gel sheet for a living body capable of efficiently penetrating carotenoids into the skin, and a sheet-shaped cosmetic using the same (Patent Literature 3) has been reported so far.

CITATION LIST

Patent Literature

Patent Literature 1

Japanese Unexamined Patent Application, First Publication No. 2013-155171

Patent Literature 2

Japanese Unexamined Patent Application, First Publication No. 2012-214454

Patent Literature 3

Japanese Unexamined Patent Application, First Publication No. 2009-73764

SUMMARY OF INVENTION

Technical Problem

However, none of the sheet-shaped external preparations of Patent Literatures 1 to 3 are effective for improving skin color of a skin color defect including dark circles around the eyes. An object of the present invention is to provide a gel composition excellent in adhesion to skin as a pack cosmetic for improving skin color.

Solution to Problem

The present invention includes the following aspects.

(1) A gel composition including: (a) at least one selected from tocopherol phosphoric acid esters and salts thereof; (b) carrageenan; (c) locust bean gum; (d) at least one selected from agar and glucomannan; and (e) water.

(2) The gel composition according to (1), further including a potassium salt.

(3) The gel composition according to (1) or (2), in which the (d) includes glucomannan.

(4) The gel composition according to any one of (1) to (3), further including xanthan gum.

(5) The gel composition according to any one of (1) to (4), in which the content of the (a) is from 0.1% to 10% by mass, the content of the (b) is from 0.5% to 1.0% by mass, the content of the (c) is from 0.3% to 0.9% by mass, and the content of the (d) is from 0.05% to 0.5% by mass.

(6) The gel composition according to any one of (1) to (5), in which the (a) is an alkali metal salt of tocopherol phosphoric acid ester.

(7) The gel composition according to (6), in which the alkali metal salt of tocopherol phosphoric acid ester is a sodium salt of tocopherol phosphoric acid ester.

(8) The gel composition according to any one of (1) to (7), which is a pack cosmetic.

(9) The gel composition according to (8), which is an eye pack cosmetic.

Advantageous Effects of Invention

According to the present invention, a gel composition excellent in adhesion to skin is provided as a pack cosmetic for improving skin color.

DESCRIPTION OF EMBODIMENTS

In one embodiment, the present invention provides a gel composition. The gel composition of the embodiment contains the following components (a) to (e).

(a) At least one selected from tocopherol phosphoric acid esters and salts thereof
(b) Carrageenan
(c) Locust bean gum
(d) At least one selected from agar and glucomannan
(e) Water

[Component (a)]

The component (a) is at least one selected from tocopherol phosphoric acid esters and salts thereof. It is confirmed that tocopherol phosphoric acid esters and salts thereof have an effect of improving skin color against dark circles around the eyes (see Japanese Unexamined Patent Application, First Publication No. 2016-50196). Accordingly, a gel composition effective for ameliorating a skin color defect such as dark circles can be obtained by blending tocopherol phosphoric acid ester or salt thereof with the gel composition.

Examples of the tocopherol phosphoric acid esters in the component (a) include compounds represented by the following General Formula (1).

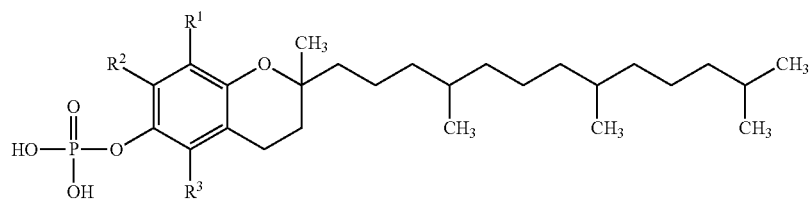

(1)

[In the formula, $R^1$, $R^2$ and $R^3$ each independently represent a hydrogen atom or a methyl group.]

Examples of the tocopherol phosphoric acid ester include, depending on $R^1$, $R^2$, and $R^3$ in General Formula (1), α-tocopherol phosphoric acid ester ($R^1$, $R^2$, and $R^3$=CH$_3$), β-tocopherol phosphoric acid ester ($R^1$ and $R^3$=CH$_3$, and $R^2$=H), γ-tocopherol phosphoric acid ester ($R^1$ and $R^2$=CH$_3$, and $R^3$=H), δ-tocopherol phosphoric acid ester ($R^1$=CH$_3$, and $R^2$ and $R^3$=H), ζ$_2$-tocopherol phosphoric acid ester ($R^2$ and $R^3$=CH$_3$, and $R^1$=H), η-tocopherol phosphoric acid ester ($R^2$=CH$_3$, and $R^1$ and $R^3$=H), and the like.

The tocopherol phosphoric acid ester for the component (a) is not particularly limited, and any of these tocopherol phosphoric acid esters may be used. Among these, α-tocopherol phosphoric acid ester and γ-tocopherol phosphoric acid ester are preferable, and α-tocopherol phosphoric acid ester is more preferable.

Since the compound represented by General Formula (1) has an asymmetric carbon atom at the 2-position of the chroman ring, there exist d-form and l-form stereoisomers, and a dl-form stereoisomer. The tocopherol phosphoric acid ester for the component (a) may be any of these stereoisomers, but the dl-isomer is preferable.

Among these, as the tocopherol phosphoric acid ester, dl-α-tocopherol phosphoric acid ester and dl-γ-tocopherol phosphoric acid ester are preferable, and dl-α-tocopherol phosphoric acid ester is more preferable.

The salt of the tocopherol phosphoric acid ester for the component (a) is not particularly limited, and examples thereof include salts with an inorganic base and salts with an organic base.

Examples of the salts with an inorganic base include alkali metal salts such as sodium salts and potassium salts; alkaline earth metal salts such as calcium salts and magnesium salts; aluminum salts; ammonium salts; zinc salts, and the like.

Examples of the salts with an organic base include alkyl ammonium salts and salts with a basic amino acid.

Among these, as the salt of tocopherol phosphoric acid ester for the component (a), an alkali metal salt is preferable, and a sodium salt is more preferable. Alkali metal salts of tocopherol phosphoric acid esters, in particular, sodium salts, have advantages such as high solubility in water and easiness in handling because of its powdery properties.

Preferred aspects of the tocopherol phosphoric acid ester for the component (a) include an alkali metal salt (e.g., a sodium salt) of a compound represented by General Formula (1), an alkali metal salt (e.g., a sodium salt) of α-tocopherol phosphoric acid ester, an alkali metal salt (e.g., a sodium salt) of γ-tocopherol phosphoric acid ester, an alkali metal salt (e.g., a sodium salt) of dl-α-tocopherol phosphoric acid ester, and an alkali metal salt (e.g., a sodium salt) of dl-γ-tocopherol phosphoric acid ester. The sodium salt of dl-α-tocopherol phosphoric acid ester is commercially available from SHOWA DENKO K.K. in the product name of TPNa (registered trademark) (labeled name: tocopheryl phosphate Na). The TPNa is exemplified as a preferred example of the component (a).

As the component (a), one selected from tocopherol phosphoric acid esters and salts thereof may be used singly, or two or more thereof may be used in combination. The component (a) preferably contains a salt of a tocopherol phosphoric acid ester, and it is more preferable to use an alkali metal salt (e.g., a sodium salt) of a tocopherol phosphoric acid ester singly.

The content of the component (a) in the gel composition of the embodiment is preferably 0.1% to 10% by mass. When the content of the component (a) is not less than the lower limit of the preferable range, the skin color improving effect of the tocopherol phosphoric acid ester or salt thereof is sufficiently exhibited. Moreover, when the content of the component (a) is not more than the upper limit of the preferable range, it is easy to take balance with other structural units, and the gel composition excellent in adhesion can be obtained.

The content of the component (a) in the gel composition of the embodiment is more preferably 0.1% to 5% by mass, still more preferably 0.5% to 3% by mass, and particularly preferably 0.7% to 2% by mass.

Tocopherol phosphoric acid esters or salts thereof can be produced by a well-known production method, for example, the method disclosed in Japanese Unexamined Patent Application, First Publication No. S59-44375, PCT International Publication No. WO 97/14705 and the like.

For example, tocopherol phosphoric acid esters can be obtained by allowing a phosphorylating agent such as phosphorus oxychloride to react with tocopherol dissolved in a solvent and appropriately performing purification after the reaction is completed. Furthermore, salts of tocopherol phosphoric acid esters can be obtained by neutralizing the obtained tocopherol phosphoric acid esters with a metal oxide such as magnesium oxide, a metal hydroxide such as sodium hydroxide, or ammonium hydroxide, or alkylammonium hydroxide.

Hereinafter, tocopherol phosphoric acid ester and salt thereof may be collectively referred to as "tocopherol phosphoric acid ester and the like".

[Component (b)]

The component (b) is carrageenan. As the carrageenan, a commercially available product can be used without any particular limitation.

Carrageenan is classified into three types, kappa-carrageenan, iota-carrageenan, and lambda-carrageenan depending on the number of sulfate groups and the presence or absence of an anhydro bond. As the carrageenan for the component (b), any one of kappa-carrageenan, iota-carrageenan, and lambda-carrageenan may be used singly, or two or more thereof may be used in combination. The carrageenan in the component (b) is preferably at least one selected from kappa-carrageenan and iota-carrageenan, and kappa-carrageenan is more preferable.

The content of the component (b) in the gel composition of the embodiment is preferably 0.5% to 1.0% by mass. When the content of the component (b) is within the preferable range, a gel composition having excellent adhesion and durability and good feeling in use as a pack cosmetic can be obtained. The content of the component (b) in the gel composition of the embodiment is more preferably 0.60% to 1.0% by mass, still more preferably 0.70% to 0.90% by mass, and particularly preferably 0.75% to 0.85% by mass.

[Component (c)]

The component (c) is locust bean gum. As the locust bean gum, a commercially available product can be used without any particular limitation.

The content of the component (c) in the gel composition of the embodiment is preferably 0.3% to 0.9% by mass. When the content of the component (c) is within the preferable range, a gel composition having excellent adhesion and durability and good feeling in use as a pack cosmetic can be obtained.

The content of the component (c) in the gel composition of the embodiment is more preferably 0.40% to 0.80% by mass, still more preferably 0.50% to 0.70% by mass, and particularly preferably 0.55% to 0.65% by mass. It is preferable that the content of the component (c) does not exceed the content of the component (b).

[Component (d)]

The component (d) is at least one selected from agar and glucomannan.

As the agar and glucomannan, a commercially available product can be used without any particular limitation.

The component (d) may be any one of agar and glucomannan, and these may be used in combination. In a case where agar and glucomannan are used in combination as the component (d), the mass ratio of agar to glucomannan is not particularly limited. For example, the mass ratio of agar:glucomannan can be set to 1:0.1 to 1:10.

The component (d) preferably contains glucomannan, and it is more preferable to use glucomannan singly. A gel composition having proper elasticity and softness can be obtained when the component (d) contains glucomannan.

The content of the component (d) in the gel composition of the embodiment is preferably 0.05% to 0.5% by mass. When the content of the component (d) is within the preferable range, a gel composition having excellent adhesion and proper elasticity can be obtained.

The content of the component (d) in the gel composition of the embodiment is more preferably 0.080% to 0.40% by mass, still more preferably 0.10% to 0.30% by mass, and particularly preferably 0.15% to 0.25% by mass.

[Component (e)]

The component (e) is water.

As the water, water having a usable grade for cosmetics such as purified water may be used. The component (e) is used as a solvent for dissolving the components (a) to (d), and optionally other components described later.

The content of water is the remaining amount of the total amount of the components (a) to (d), and optionally other components described later.

[Other Components]

The gel composition of the embodiment may contain other components in addition to the components (a) to (e). Examples of other components include alkali metal salts, xanthan gum, and polyhydric alcohols.

(Alkali Metal Salts)

The gel composition of the embodiment preferably contains an alkali metal salt (excluding alkali metal salts of tocopherol phosphoric acid esters). By containing an alkali metal salt, the durability of the gel composition is improved.

Examples of the alkali metal salts include sodium salts and potassium salts. Among these, potassium salts are preferable. By using potassium salts as the alkali metal salt, the durability is further improved.

Examples of the alkali metal salts include chloride salts, sulfate salts, and phosphate salts, and the chloride salts are preferable. For example, potassium chloride and sodium chloride are preferable, and potassium chloride is more preferable.

One alkali metal salt may be used singly, or two or more thereof may be used in combination.

In a case where the gel composition of the embodiment contains an alkali metal salt, the content of the alkali metal salt in the gel composition is preferably 0.01% to 2% by mass. When the content of the alkali metal salts is within the preferable range, a gel composition having excellent durability and proper softness can be obtained.

The content of the alkali metal salt in the gel composition of the embodiment is more preferably 0.03% to 1% by mass, still more preferably 0.05% to 0.5% by mass, and particularly preferably 0.1% to 0.3% by mass.

(Xanthan Gum)

The gel composition of the embodiment preferably contains xanthan gum.

By containing xanthan gum, adhesion and durability of the gel composition are improved, and the feeling in use as a pack cosmetic is also improved.

As the xanthan gum, a commercially available product can be used without any particular limitation.

In a case where the gel composition of the embodiment contains xanthan gum, the content of the xanthan gum in the gel composition is preferably 0.05% to 0.3% by mass. When the content of the xanthan gum is within the preferable range, a gel composition having excellent adhesion and durability and good feeling in use as a pack cosmetic can be obtained.

The content of the xanthan gum in the gel composition of the embodiment is more preferably 0.080% to 0.30% by mass, still more preferably 0.10% to 0.20% by mass, and particularly preferably 0.12% to 0.18% by mass.

(Polyhydric Alcohol)

The gel composition of the embodiment may contain polyhydric alcohol. The polyhydric alcohol functions as a moisturizing component. Examples of the polyhydric alcohol include dihydric alcohol such as ethylene glycol, propylene glycol, 1,3-butylene glycol, ethylene glycol monobutyl ether, diethylene glycol, triethylene glycol, 1,4-butylene glycol, dipropylene glycol, 1,2-hexanediol, and pentylene glycol; trihydric alcohol such as glycerin and trioxyisobutane; tetrahydric alcohol such as erythritol and pentaerythritol; pentahydric alcohol such as xylitol and adonitol; hexahydric alcohol such as allodulcitol, sorbitol, sorbitol solution, and mannitol; and polyglycerin.

Among these, as the polyhydric alcohol, dihydric alcohols such as 1,2-hexanediol and pentylene glycol, and trihydric alcohols such as glycerin are preferable. One polyhydric alcohol may be used singly, or two or more thereof may be used in combination. In a preferred aspect, the dihydric alcohol and trihydric alcohol are used in combination as the polyhydric alcohol. In the above, pentylene glycol is preferable as the dihydric alcohol, and glycerin is preferable as the trihydric alcohol. In a case where the dihydric alcohol and the trihydric alcohol are used in combination as the polyhydric alcohol, the mass ratio of the dihydric alcohol to the trihydric alcohol is not particularly limited. For example, the mass ratio of the dihydric alcohol:trihydric alcohol is 1:1 to 1:20, and more preferably 1:2 to 1:10.

In a case where the gel composition of the embodiment contains the polyhydric alcohol, the content of the polyhydric alcohol in the gel composition is preferably 1% to 30% by mass. When the content of the polyhydric alcohol is within the preferable range, a gel composition having proper water retaining properties and moisturizing properties can be obtained.

The content of the polyhydric alcohol in the gel composition of the embodiment is more preferably 5% to 20% by mass, still more preferably 8% to 20% by mass, and particularly preferably 10% to 15% by mass.

(Others)

In addition to the components listed above, the gel composition of the embodiment can contain any components generally used for a cosmetic as long as the effects of the present invention are not impaired.

Examples of such components include preservatives, antibacterial agents, whitening agents, vitamins and derivatives thereof, antiphlogistic agents, anti-inflammatory agents, blood circulation promoters, hormones, anti-wrinkle agents, anti-aging agents, tightening agents, cooling sensation agents, warming sensation agents, wound healing promoters, stimulus relaxation agents, analgesic agents, cell activators, plant/animal/microbe extracts, antipruritic agents, exfoliating/dissolving agents, astringents, enzymes, nucleic acids, fragrances, pigments, coloring agents, anti-inflammatory analgesics, antifungal agents, antihistamines, antibiotics, antibacterial substances, herbal medicines, antipruritics, keratin softening and peeling agents, antiseptic disinfectants, antioxidants, pH adjusters, and additives. Specific examples of these components include those disclosed in, for example, Japanese Unexamined Patent Application, First Publication No. 2016-50196. One of the other components may be used singly, or two or more thereof may be used in combination.

Examples of the preservative include benzoic acid, sodium benzoate, undecylenic acid, salicylic acid, sorbic acid, potassium sorbate, dehydroacetic acid, sodium dehydroacetate, isobutyl parahydroxybenzoate, isopropyl parahydroxybenzoate, and ethyl parahydroxybenzoate, butyl parahydroxybenzoate, propyl parahydroxybenzoate, benzyl parahydroxybenzoate, methyl parahydroxybenzoate, sodium methyl parahydroxybenzoate, phenoxyethanol, photosensitive element 101, photosensitive element 201, and photosensitive element 401. One preservative may be used singly, or two or more thereof may be used in combination. Phenoxyethanol is exemplified as a preferable preservative.

Examples of the pH adjuster include citric acid, sodium hydroxide, potassium hydroxide, and triethanolamine. One pH adjuster may be used singly, or two or more thereof may be used in combination. Citric acid is exemplified as a preferable pH adjuster.

The pH of the gel composition of the embodiment is preferably 6.0 to 8.5. When the pH is within the preferable range, stability of the tocopherol phosphoric acid ester or salt thereof is satisfactory and stability of the gel composition is improved. In addition, in a case where the gel composition is used as a pack cosmetic, irritation to the skin can be reduced. The pH of the gel composition of the embodiment is more preferably 6.0 to 8.0, and still more preferably 6.5 to 7.6. The pH is a value at the temperature of 25° C. and can be measured with a pH meter.

The pH of the gel composition of the embodiment can be adjusted using a pH adjuster.

The gel composition of the embodiment can be produced by mixing the components (a) to (e) and optionally adding and mixing other components. The specific example of the production method of the gel composition of the embodiment is described below.

First, an aqueous solution containing the component (a) (solution A) and an aqueous solution containing the components (b) to (d) (solution B) are prepared. Next, after the solution B is heated to about 80 to 95° C., the solution A is added thereto and other components are optionally added and mixed. Then, the gel composition of the embodiment can be obtained by cooling the mixed solution.

In a case where the gel composition of the embodiment is a pack cosmetic, the mixed solution may be put into a desired pack-shaped mold and cooled. Thereby, the pack cosmetic of the desired shape which is composed of the gel composition of the embodiment can be produced.

The gel composition of the embodiment can be suitably used as a pack cosmetic. Since the gel composition of the embodiment contains a tocopherol phosphoric acid ester and the like as the component (a), the gel composition has an effect of improving skin color such as dark circles around the eyes. In addition, since the gel composition of the embodiment contains the components (b) to (d), the gel composition has sufficient adhesion to the skin as a pack cosmetic. Therefore, by applying the gel composition of the embodiment as a pack cosmetic to the site of the skin color defect, the skin color improvement effect at the site can be expected. The gel composition of the embodiment is particularly useful as an eye pack cosmetic for ameliorating dark circles around the eyes.

By using the gel composition of the embodiment as a pack cosmetic, it is possible to allow the tocopherol phosphoric acid ester and the like to efficiently penetrate into the skin.

Although the skin color improvement effect of the tocopherol phosphoric acid ester and the like have been confirmed in the related art, a gel composition that contains the tocopherol phosphoric acid ester and the like and can be used as a pack cosmetic has not been known. In order to use the gel composition as a pack cosmetic, adhesion to the skin is required. In particular, for the pack cosmetic with a small contact area to the skin, such as an eye pack cosmetic, if the adhesion of the pack cosmetic is low, the pack cosmetic falls off from the skin.

According to the invention, a gel composition having high adhesion to the skin can be obtained by combining the components (b) to (d) with the component (a). Therefore, the gel composition can be suitably used for a pack cosmetic with a small contact area to the skin such as an eye pack cosmetic.

EXAMPLES

Hereinafter, the invention will be described by using Examples, but the invention is not limited to the following Examples.

[Production of Gel Composition]

Gel compositions of Examples 1 to 5 and Comparative Example 1 were produced according to the compositions shown in Table 1. The unit of the numbers shown in Table 1 is the % by mass on the basis of the mass of each gel composition.

First, the materials shown in Table 1 were respectively dissolved in purified water to prepare a solution A, solution B, and solution C. Subsequently, the solution B was heated to 85 to 90° C., and then the solution A and the solution C were added to the solution B. Subsequently, a mixture of the solutions A to C was stirred with a homomixer, and then put into an eye pack mold and cooled to obtain the gel compositions of Examples 1 to 5 and Comparative Example 1. The gel compositions of Examples 1 to 5 and Comparative Example 1 were all within the range of pH 6.5 to 7.6.

TABLE 1

| Solution | Materials | Example 1 | Example 2 | Example 3 | Example 4 | Example 5 | Comparative Example 1 |
|---|---|---|---|---|---|---|---|
| A | Tocopheryl phosphate Na | 1 | 1 | 1 | 1 | 1 | 1 |
|   | Pentylene glycol | 3 | 3 | 3 | 3 | 3 | 3 |
|   | 1% Citric acid | Proper amount | Proper amount | Proper amount | Proper amount | Proper amount | Proper amount |
|   | Phenoxyethanol | 0.6 | 0.6 | 0.6 | 0.6 | 0.6 | 0.6 |
| B | Carrageenan | 0.8 | 0.8 | 0.8 | 0.8 | 0.8 | 0.8 |
|   | Locust bean gum | 0.6 | 0.6 | 0.6 | 0.6 | 0.6 | 0.6 |
|   | Xanthan gum |  | 0.15 | 0.15 |  |  | 0.15 |
|   | Agar | 0.2 |  |  | 0.2 |  |  |
|   | Glucomannan |  | 0.1 | 0.2 |  | 0.2 |  |
|   | Glycerin | 10 | 10 | 10 | 10 | 10 | 10 |
| C | 1% Potassium chloride |  |  | 16 | 10 | 16 | 16 |
|   | 5% Sodium chloride | 10 | 10 |  |  |  |  |
|   | Purified water | Residual amount | Residual amount | Residual amount | Residual amount | Residual amount | Residual amount |
|   | Total | 100 | 100 | 100 | 100 | 100 | 100 (% by mass) |

The following materials were used for each material in Table 1.
Carrageenan GENUGEL (registered trademark) CG-130 (CP Kelco)
Locust bean gum GENUGUM (registered trademark) RL-200Z (CP Kelco)
Xanthan gum KELTROL CG-BT (CP Kelco)
Glucomannan Leox (registered trademark) ONE (Shimizu Chemical Corporation)
Tocopheryl phosphate Na (sodium salt of dl-α-tocopherol phosphoric acid ester: TPNa (registered trademark) (SHOWA DENKO K.K.))

[Adhesion Test]
The gel compositions of Examples 1 to 5 and Comparative Example 1 were applied to the back of the hand, the hand was held still in a state where the palm faces upward, and the time taken for the gel composition to drop off from the back of the hand was measured.
The results are shown in Table 2.

TABLE 2

|  | Time taken for the gel composition to drop off (Seconds) |
|---|---|
| Example 1 | 6 |
| Example 2 | 19 |
| Example 3 | 60 or more |
| Example 4 | 60 or more |
| Example 5 | 14 |
| Comparative Example 1 | 0 |

It was confirmed that all of the gel compositions of Examples 1 to 5 are adhered to the skin. In particular, it was confirmed that the gel compositions of Examples 3 and 4 have high adhesion.
In contrast, the gel composition of Comparative Example 1 immediately dropped off from the back of the hand and did not have adhesion. Therefore, it was shown that the gel composition of Comparative Example 1 is not suitable for use as an eye pack cosmetic.

[Durability Test]
The gel compositions of Examples 1 to 5 and Comparative Example 1 were lifted to be in a vertical state for one minute, and the variation amount in length in the direction of gravity from the state before the gel composition was lifted was measured.
The results are shown in Table 3. In Table 3, "+" indicates the elongated length of the gel composition as compared to the state before lifting. It can be determined that as the variation amount of + is smaller, the durability is higher.

TABLE 3

|  | Variation amount (cm) |
|---|---|
| Example 1 | Dropped off during the test, Not measurable |
| Example 2 | +1.5 |
| Example 3 | +0 |
| Example 4 | +1 |
| Example 5 | +0.5 |
| Comparative Example 1 | +0.5 |

Among the gel compositions of Examples 1 to 5 and Comparative Example 1, the gel composition of Example 3 had the highest durability.

[Panelist Test 1]
Five panelists used the gel compositions of Examples 1 to 5 and Comparative Example 1 as an eye pack cosmetic and evaluated the feeling in use thereof. The evaluation was performed for each evaluation item by the respective panelists giving evaluation scores according to the criteria in Table 4. Table 5 shows the total points of the evaluation scores of the five panelists.

TABLE 4

| Evaluation | Evaluation score |
|---|---|
| Very bad | 1 |
| Bad | 2 |
| Normal | 3 |

TABLE 4-continued

| Evaluation | Evaluation score |
|---|---|
| Good | 4 |
| Very good | 5 |

TABLE 5

| | Adhesion | Proper elasticity | Easy to peel off | Easy to take out from the container |
|---|---|---|---|---|
| Example 1 | 19 | 17 | 18 | 14 |
| Example 2 | 14 | 15 | 17 | 14 |
| Example 3 | 22 | 23 | 21 | 21 |
| Example 4 | 19 | 20 | 20 | 19 |
| Example 5 | 17 | 17 | 18 | 17 |
| Comparative Example 1 | 12 | 19 | 20 | 17 |

As for the adhesion, the evaluation score of Comparative Example 1 was the worst as with the above adhesion test. The gel composition of Example 3 had the highest evaluation score in every evaluation item.

[Panelist Test 2]

In the same manner as the panelist test 1, five panelists used the gel compositions of Examples 1 to 5 and Comparative Example 1 as an eye pack cosmetic and evaluated the ease of collapse for the gel compositions. The evaluation was performed by the respective panelists giving evaluation scores according to the criteria in Table 6.

Table 7 shows the total points of the evaluation scores of the five panelists. In Table 7, a higher score means that the evaluation is bad.

TABLE 6

| Evaluation | Evaluation Score |
|---|---|
| Do not feel | 1 |
| ↓ | 2 |
| | 3 |
| | 4 |
| Feel | 5 |

TABLE 7

| | Easy to collapse |
|---|---|
| Example 1 | 16 |
| Example 2 | 10 |
| Example 3 | 5 |
| Example 4 | 11 |
| Example 5 | 10 |
| Comparative Example 1 | 11 |

Among Examples 1 to 5 and Comparative Example 1, it was shown that the gel composition of Example 3 has the best evaluation and is unlikely to collapse.

From the results, it was shown that the gel composition of Comparative Example 1 has poor adhesion and is not suitable for use as an eye pack cosmetic. The gel compositions of Examples 1 to 5 can be used as an eye pack cosmetic from the viewpoint of adhesion. Among these, the gel compositions of Examples 3 to 5 were preferred from the viewpoint of durability. In all the evaluation items, the gel composition of Example 3 showed the best evaluation, indicating that the gel composition of Example 3 can be satisfactorily used as a gel composition for an eye pack cosmetic.

INDUSTRIAL APPLICABILITY

According to the present invention, a gel composition that can be used as a pack cosmetic for improving skin color is provided. The gel composition provided by the present invention is particularly useful as a pack cosmetic such as an eye pack cosmetic.

The invention claimed is:

1. A gel composition comprising:
   (a) at least one selected from tocopherol phosphoric acid esters and salts thereof;
   (b) carrageenan;
   (c) locust bean gum;
   (d) at least one selected from agar and glucomannan; and
   (e) water.

2. The gel composition according to claim 1, further comprising a potassium salt.

3. The gel composition according to claim 1, wherein the (d) comprises glucomannan.

4. The gel composition according to claim 1, further comprising xanthan gum.

5. The gel composition according to claim 1, wherein the content of the (a) is 0.1% to 10% by mass, the content of the (b) is 0.5% to 1.0% by mass, the content of the (c) is 0.3% to 0.9% by mass, and the content of the (d) is 0.05% to 0.5% by mass.

6. The gel composition according to claim 1, wherein the (a) is an alkali metal salt of tocopherol phosphoric acid ester.

7. The gel composition according to claim 6, wherein the alkali metal salt of tocopherol phosphoric acid ester is a sodium salt of tocopherol phosphoric acid ester.

8. The gel composition according to claim 1, which is a pack cosmetic.

9. The gel composition according to claim 8, which is an eye pack cosmetic.

10. The gel composition according to claim 1, further comprising pentylene glycol.

11. The gel composition according to claim 10, further comprising glycerin.

12. The gel composition according to claim 1, further comprising a potassium salt and xanthan gum, wherein the (d) comprises glucomannan.

13. The gel composition according to claim 12, wherein the potassium salt is potassium chloride.

14. The gel composition according to claim 1, wherein the pH is in the range of 6.0 to 8.5.

* * * * *